United States Patent
Williams et al.

(10) Patent No.: US 9,662,303 B2
(45) Date of Patent: May 30, 2017

(54) COMPOSITION AND METHOD FOR TREATING CANCER

(75) Inventors: Lawrence A.D. Williams, St. Catherine (JM); H. George Levy, Royal Oak, MI (US)

(73) Assignee: PG-Pharma, LLC, Monroe, MI (US)

( * ) Notice: Subject to any disclaimer, the term of this patent is extended or adjusted under 35 U.S.C. 154(b) by 0 days.

(21) Appl. No.: 11/804,514

(22) Filed: May 18, 2007

(65) Prior Publication Data
US 2008/0070839 A1 Mar. 20, 2008

Related U.S. Application Data

(60) Provisional application No. 60/825,843, filed on Sep. 15, 2006, provisional application No. 60/919,601, filed on Mar. 24, 2006.

(51) Int. Cl.
*A61K 31/105* (2006.01)
*A61K 38/38* (2006.01)
*A61K 47/48* (2006.01)

(52) U.S. Cl.
CPC ............ *A61K 31/105* (2013.01); *A61K 38/38* (2013.01); *A61K 38/385* (2013.01); *A61K 47/48284* (2013.01)

(58) Field of Classification Search
None
See application file for complete search history.

(56) References Cited

U.S. PATENT DOCUMENTS

2005/0261321 A1* 11/2005 Xu et al. ............... 514/269

OTHER PUBLICATIONS

Williams et al. (West Indian Medical J. Jan. 2007, 56 (1): 17-21).*
Williams et al. (Recent Research Developments in Phytochemistry 2002, 6: 13-68)t.*
Williams et al. (Recent Research Developments in Phytochemistry 2002, 6:13-68).*
Benzyl Trisulfide (National Center for Biotechnology Information. PubChem Compound Database; CID=122842, https://pubchem.ncbi.nlm.nih.gov/compound/122842 (accessed Sep. 26, 2016).*
Albumin from Bovine Serum (Sigma-Aldrich, Product Information May 2, 2000).*

* cited by examiner

*Primary Examiner* — Peter J Reddig
(74) *Attorney, Agent, or Firm* — Stefan J. Kirchanski; Zuber Lawler & Del Duca, LLP

(57) ABSTRACT

The present invention provides a compound for treating cancer including an isolated form of dibenzyl trisulfide (DTS) provided in an effective amount to act as an agent against human diseases, including various forms of cancer. The present invention also provides a compound for treating cancer including DTS isolated from *Petiveria alliacea* L. (guinea hen weed) for providing an effective, potent anti-proliferation and/or cytotoxic activity on a wide range of cancer cell lines. The present invention further provides DTS derivatives (e.g. DTS-albumin complexes) in effective dosage for providing a potent anti-proliferation and/or cytotoxic activity on a wide range of cancer cell lines. Additionally, the present invention provides methods of isolating and/or providing the DTS and/or its derivatives in an effective amount for providing a potent anti-proliferation and/or cytotoxic activity on cancer cell lines.

8 Claims, 1 Drawing Sheet

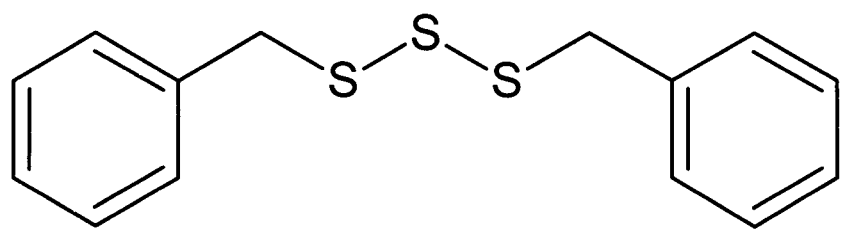

US 9,662,303 B2

COMPOSITION AND METHOD FOR TREATING CANCER

CROSS-REFERENCE TO RELATED APPLICATIONS

This application claims the benefit of the following provisional applications, U.S. Provisional Patent Application Ser. No. 60/825,843 filed Sep. 15, 2006, and U.S. Provisional Patent Application Ser. No. 60/919,601, filed Mar. 24, 2006, which are incorporated herein by reference in their entirety.

BACKGROUND OF THE INVENTION

1. Field of the Invention

The present invention relates generally to the treatment of various disease states with Dibenzyl Trisulphide (DTS). Further, the present invention relates to the use of DTS for cancer therapeutic treatment.

2. Description of the Prior Art

The urgent need to find effective and safe therapeutic agents to treat cancers and auto-immune diseases such as Type 1 diabetes, lupus erythematosus, rheumatoid arthritis and multiple sclerosis has been one of the greatest challenges for the pharmaceutical companies (1). Recent studies have revealed that the top 150 propriety drugs used in the western hemisphere, 57% contained at least one major active compound derived from natural sources (2). However, one of the major foci of the therapeutic industry is to find small molecules which regulate the biochemistry of disease cells via signal transduction modes of action (3), dibenzyl trisulphide (DTS) is one such molecule (see FIG. 1). Dibenzyl trisulphide was first coded as DBTS when its insecticidal/repellent activities were discovered (4) and re-coded as DTS when its therapeutic potential was found (5). The signal transduction pathways regulate cell biological processes e.g. gene expression, differentiation, cell division and apoptosis generated from interaction/binding of molecules to cell membrane receptors. One of the most intensely investigated therapeutic signal transduction pathway is that which regulates the process of apoptosis or programmed cell death. The apoptotic signal transduction cascade is implicated in several cancers, Alzheimer's, Parkinson's, transplant rejection, autoimmune disorder such as diabetes, acquired immune deficiency syndrome and Hodgkin's lymphoma (6).

The prior art includes US Pub. No. 2005/0261321, "Substituted organosulfur compounds and methods of using thereof." This published patent application generally describes using DTS to treat cancer. It also generally mentions DTS formulated with bovine serum albumin, without any cytotoxic evaluation, summarizing Rosner et al. (7). Lastly the application describes using various R groups attached to a carbon molecule connecting the trisulfide to a benzyl group.

U.S. Pat. No. 6,555,712 as relevant to the possible use of DTS and its substituted cousins as therapeutic agents. The patent, entitled "Process for the preparation of diorganotrisulfide," provides a general method for synthesizing various diorganotrisulfides, including DTS and its substituted cousins.

An article entitled "Synthesis and anti anti-tumor evaluation of new trisulfide derivatives," was written by H. An, J. Zhu, X. Wang, and X. Xu and was published in Bioorganic & Medicinal Chemistry Letters, Volume 16, Issue 18, pages 4826-4829 (September 2006). The article reported information on the anti-tumor activities of DTS and several related species (involving substitution of at least one benzyl ring from the base DTS molecule).

However, none of the above formulations or methods of using DTS created an enhanced cytotoxic effect against cancer cells; thus there remains a need for such a molecule to more affectively treat cancer, among other ailments.

The present invention is provided to solve the problems discussed above and other problems. A full discussion of the features and advantages of the present invention is deferred to the following detailed description, which proceeds with reference to the accompanying drawings.

SUMMARY OF THE INVENTION

A first aspect of the present invention is to provide dibenzyl trisulfide (DTS), particularly as a naturally-occurring therapeutic agent against human diseases, including various forms of cancer. Another aspect of the present invention is to provide DTS isolated from *Petiveria alliacea* L. (guinea hen weed) for providing an effective, potent anti-proliferation and/or cytotoxic activity on a wide range of cancer cell lines. Yet another aspect of the present invention includes providing DTS derivatives in effective dosage for providing a potent anti-proliferation and/or cytotoxic activity on a wide range of cancer cell lines. Still another aspect of the present invention includes methods of isolating and/or providing the DTS and/or its derivatives in an effective amount for providing a potent anti-proliferation and/or cytotoxic activity on cancer cell lines.

These and other aspects of the present invention will become apparent to those skilled in the art after a reading of the following description of the preferred embodiment.

BRIEF DESCRIPTION OF THE DRAWINGS

FIG. 1 is a graphical representation of a DTS molecule according to the present invention.

DETAILED DESCRIPTION

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms. The description below is for the purpose of describing a preferred embodiment of the invention and is not intended to limit the invention thereto.

Also, throughout this document, numbers in parenthesis (e.g. "(31)") represent published references which can be found and correlated to the numbers at the end of this document. When used, a number in parenthesis represents that the correlating reference supports at least partially, but not necessarily entirely, the assertion in the sentence or the clause immediately preceding the number.

The present invention provides a compound for treating cancer including an isolated form of dibenzyl trisulfide (DTS) provided in an effective amount to act as an agent against human diseases, including various forms of cancer. The present invention also provides a compound for treating cancer including DTS isolated from *Petiveria alliacea* L. (guinea hen weed) for providing an effective, potent anti-proliferation and/or cytotoxic activity on a wide range of cancer cell lines. The present invention further provides DTS derivatives in effective dosage for providing a potent anti-proliferation and/or cytotoxic activity on a wide range of cancer cell lines. Additionally, the present invention provides methods of isolating and/or providing the DTS and/or its derivatives in an effective amount for providing a potent anti-proliferation and/or cytotoxic activity on cancer cell lines.

Dibenzyl trisulfide (hereafter DTS) has the molecular structure shown in FIG. 1. The present invention contemplates that DTS is a polysulphide mitogen with a wide range of therapeutic implication in the field of medicine and biochemistry. The molecule signals via the MAPkinase (erk1/erk 2) pathway.

The present invention contemplates that DTS in general causes hyperphosphorylation which can lead to many beneficial effects, including its affect on Cadherin 5, which can lead to enhanced anti-cancer activity. Upregulation of Caherin-5 thru hyper-phosphorylation regulates the gap junction which is likely to reduce metastasis of cancer.

DTS can be extracted from a plant (Petiveria alliacea); it can also be synthesized in the laboratory. DTS has anticancer activity and acts to stimulate the production of stem cells from bone marrow and thymus with little toxic effect. DTS has been shown to inhibit growth of numerous cancer cells, including SH-SY5Y neuroblastoma, MCF-7 Mammary Carcinoma, IPC-melanoma, TE-671 Sarcoma, A549 lung cancer, leukemia, and lymphorma. The inhibition mechanism is understood presently to be through microtubule disruption and induced apoptosis. DTS also alters the immunogenicity of antigens through binding with the tyrosine residues in the antigens. It activates stem cells leading to the production of blood and bone marrow cells, with an increased level of phagocytes.

Implication of DTS in the Treatment of Cancers.

The anti-proliferation/cytotoxic activity of DTS was first discovered by Rosner's group (7) using the human SH-SY5Y neuroblastoma cells, while the cell differentiation effects on HL-60 promyelocytic cells was reported (8). Subsequently, the $IC_{50}$ values in μM concentrations (data in parentheses) were reported for DTS on several human cancer cell lines using different bioassay techniques (9,10); SH-SY5Y neuroblastoma (0.43 μM) (9), MCF-7 mammary carcinoma (2.24 μM and 6.6 μM) (9;10); IPC-melanoma (2.90 μM) (9); A549 small cell lung cancer (15.85 μM) (9); A637 primary bladder carcinoma (18.84 μM) (9); Jurkat leukaemia (0.35 μM) (10); ovarian A2780 and OVCAR4 (0.40 μM and 1.4 μM, respectively) (10); fibrosarcoma HT1080 (1.9 μM) (10); non-small cell lung cancer H460 (5.1 μM) (10); breast M231 (2.4 μM) (10); adenocarcinoma HeLa (2.5 μM) (10). In addition, it was reported that 0.56 μM of DTS gave 44.67% anti-proliferation/cytotoxic activity on the human TE-671 sarcoma cell line (9). The cytotoxic action of DTS on the human SH-SY5Y neuroblatsoma cell lines was enhanced by complexing DTS to Bovine Serum Albumin by 70 fold in vitro (11;12).

The present invention, using DTS-albumin and more specifically DTS-BSA complexes, provides enhancement in cytotoxicity up to about 2000 fold over DTS alone, as shown from experiments outlined below. Based on modes of action studies DTS could be useful against prostate cancers for the following reasons; DTS was found to enhance the binding of mitogen-activated protein kinases phosphatase 1 (MKP-1) to its substrate 3-O-methyl-fluorescein phosphate cyclohexyl ammonium salt (OMFP) in vitro (12). MKP-1 is a dephosphorylator of various MAPkinases including extracellur regulated kinases 1 and 2 (erk1/2) (13). It is known that in prostate cancers the phosphorylation of erk 1/2 are dramatically increased, up to 1600% have been reported (14). Thus, if DTS enhanced the activity of the dephosphorylator MKP-1 it could be implicated in the treatment of prostate cancers, as a possible down regulator of the phosphorylation on erk1/2. In addition, MKP-1 is now recognized as a potential therapeutic target in cancer chemotherapy (15). IPC-melanoma cells exposed to 1.0 μM of DTS undergo nuclear fragmentation to produce micronuclei, indicating mitotic catastrophe (9). The fragmentation of nucleus in cells exposed to cytotoxic agents is one of the diagnostic features of apoptosis. DTS has a strong binding affinity for albumin and RBCs, thus it may have implications for the treatment of cancers in the central nervous system. These findings indicate that DTS could be instrumental in cancer chemotherapy.

DTS can be derived several different ways. Preferably, according to the present invention, it is chemically synthesized. Alternatively, it can be isolated from Petiveria alliacea L (the guinea hen weed).

Preferably, according to the present invention, DTS is bound to an albumin (e.g. bovine serum albumin, BSA), and is synthesized as follows to create the DTS-BSA complex:

1. Prepare a 0.05% (w/v) stock solution of dibenzyl trisulphide (DTS) in methanol i.e. 5.0 mg of DTS in 10 mL of methanol.

2. Prepare a 0.2% stock solution of Bovine Serum Albumin (BSA) in Tris acetate buffer pH 6.75, i.e. 2.0 mg BSA in 1.0 mL of the Tris buffer.

3. Combine the DTS solution from step 1 with the BSA solution from step 2 in a ratio of 1:10 (DTS:BSA; v/v) e.g. 50 μL DTS to 500 μL BSA, and incubate for 12 hours at 7° C. in a low temperature refrigerator. NOTE: methanol will not distort the molecular configuration of albumins at concentrations less than 30% (v/v).

4. Add 10 μL of the DTS:BSA mixture from above to cells in culture in 1.0 mL of culture medium. See Williams et al., (2004) West Indian Medical Journal 53 (4) pp. 208-219 for the preparation of cell culture medium and assessment of anti-proliferation/cytotoxic activity on the human SH-SY5Y neuroblatsoma cells (12); the previous reference is hereby incorporated by reference in its entirety.

A summary of the results from an experiment involving the above synthesis method were as follows:

1. BSA in Tris acetate buffer at 1.0 mg/mL gave −2.72% anti-proliferation activity (i.e. it was a slight stimulator for the growth of the cells).

2. Tris acetate buffer pH 6.75 (10 μL/mL) gave 0.4% anti-proliferation activity. DTS at 50-0.5 ng/mL+BSA (1.0 mg/mL) gave an average of 92.11% anti-proliferation activity, at 0.05 ng/mL DTS+BSA anti-proliferation activity was lost.

3. DTS at 78 ng/mL (No BSA) gave 38.22% anti-proliferation activity.

4. DTS at 39 ng/mL (No BSA) gave 1.68% anti-proliferation activity.

Below, in Table 1, titled "Anti-proliferation/cytotoxic activity of dibenzyl trisulphide (DTS) and Bovine serum albumin complex", are the tabulated results from the above experiment.

TABLE 1

| Samples | Percentage anti-proliferation activity |
| --- | --- |
| DTS at 50-0.5 ng/mL + BSA | 90.00 to 92.11% |
| DTS at 1.25 μg/mL (No BSA) | 93.00% |
| DTS at 78 ng/mL (No BSA) | 38.22% |
| DTS at 39 ng/mL (No BSA) | 1.68% |
| BSA at 1.0 mg/mL | −2.72% |

TABLE 1-continued

| Samples | Percentage anti-proliferation activity |
|---|---|
| BSA in Tris-acetate buffer | (slightly stimulatory) |
| Tris acetate buffer alone | 0.4% |

From Table 1, the activity of DTS without BSA at 1.25 μg/mL (1250 ng/mL) is not significantly different from the anti-proliferation activity of DTS with BSA at 0.5 ng/mL. Thus, the enhancement in anti-proliferation activity is 1250 divided by 0.5, which equals 2500 fold.

Synthesizing DTS-BSA using the above steps causes DTS-BSA to have an unexpected and surprising enhancement in cytotoxic activity toward cancer cells. Doing such enhances the cytotoxic activity of DTS between 100 to 2500 fold on human SH-SY5Y neuropblastoma cells in vitro; as seen from the results from. The present invention contemplates that this enhanced activity is due to the specific bonding configuration and sites between DTS and albumin (e.g. bovine serum albumin).

According to the preferred embodiment of the present invention, the steps described above create a specific DTS-BSA molecule that results in the enhanced cytotoxic activity mentioned above. In the DTS-BSA complex of the present invention, the hydroxyl of tyrosine amino acid in the BSA binds to the central sulphur atom of the trisulphide bridge in DTS (11). Generally DTS binds to an aromatic region of BSA (7). This region is rich in tyrosine residue and also has phenylalanine which is also an aromatic amino acid. The present invention's preferred synthesis steps described above result in DTS being bound to BSA at the hydroxyl of tyrosine in the BSA. Likewise the present invention's preferred synthesis steps result in the BSA being bound to DTS at the central sulphur atom of the trisulphide bridge in DTS.

According to the present invention, spectrophotometric absorbance binding experiments on pure tyrosine and phenylalanine were conducted and found that DTS binds only to tyrosine. Here is an outline of these experiments:

1. A plot of Absorbance (nm) with time (mins) of the interaction with tyrosine and DTS gives a normal distribution (Gaussian) with the highest optimum at room temperature.

2. As temperature is increased there is a lowering of the optimum on the graph until a straight line is created.

3. These experiments suggest that slight increases in temperature will break the hydrophobic bonds in the interaction between DTS and tyrosine.

4. Phenylalanine, which is an aromatic amino acid, gives a straight line at room temperature with DTS, while DTS and tyrosine give a Gaussian distribution; the height of the curve is a function of the ratio of the DTS used.

5. Thus, the absence of a Gaussian distribution with DTS and phenylalanine and the presence of the Gaussian distribution with DTS and tyrosine indicate that when DTS-BSA is synthesized according to the present invention, the DTS binds only to tyrosine on BSA.

Additionally, tyrosine is a signal transduction activation amino acid, while phenylalanine is not. Thus, the present invention contemplates that the MAP kinase signaling is emerging from the interaction of the DTS with the tyrosine residue in the receptors.

Further, the present invention contemplates that DTS will bind to any proteins or peptides that contained tyrosine (e.g. human serum albumin or bovine serum albumin) or peptides (e.g. pokeweed anti-viral proteins (PAPS), and monoclonal anti-bodies for immuno-thrapeutic applications (to produce new drugs). Thus, the present invention contemplates that DTS binds hydrophobically to the tyrosine residues of peptides or proteins and may produce new drugs (because DTS binds to pure tyrosine amino acid). Any peptide or protein containing tyrosine DTS should interact or bind to these molecules which could lead to the formulation of other drugs. Also, DTS binds readily to red blood cells (RBCs) without lysis. Thus, DTS can cross the blood-brain barrier probably by being bound to a carrier protein (e.g. albumin) or on RBCs making it ideal for treating tumors and other diseases of the central nervous system.

The present invention provides an anti-cancer treatment method that includes, but is not limited to, the following steps. First, an organosulfur composition having dibenzyl trisulfide (DTS) is provided that is formulated to be bound to an albumin. Second, the DTS bound to the albumin is formulated to have an increased cytotoxic activity toward cancer cells on the order of about at least 100 times greater than the cytotoxic activity of DTS without albumin. Third, the DTS-albumin is administered to a patient suffering from cancer (and having cancer cells) in a therapeutically effective amount.

Preferably the albumin is BSA, thereby creating a DTS-BSA formulation. Alternatively, the albumin could be human serum albumin (HSA), or other albumins. When bound to BSA, the present invention provides increased cytotoxic activity toward cancer cells on the order of between about 100 times and about 2500 times greater than the cytotoxic activity of DTS without BSA.

The DTS-albumin formulation of the present invention can be administered to a patient in a variety of different ways. The administration includes intravenous administration, oral administration, topical administration, parenteral administration, and targeted administration to the cancer cells (e.g. direct injection into a cancerous mass or by molecular selectivity for markers on cancer cells, etc.). Preferably, the administration is intravenous.

The DTS-albumin formulation of the present invention can also be administered to a patient with a formulation dosage that is predetermined based upon data specific to that patient. For example, weight, metabolic factors, genetic factors, etc. can contribute to varying predetermined dosage amounts that are used to prescribe the specific predetermined dosage to the patient. Preferably the formulation dosage is between about 0.023 mg/kg and about 2.3 mg/kg body weight. The doses were calculated based on a DTS dose of 11 mg/kg body weight which stimulated the immune system in mice which was then co-related to a 240 ng/mL the effective in vitro dose. The DTS-BSA complex was active at 0.5 ng/mL in vitro dose, a ratio of about 480. Thus, 11 divided by 480 is about 0.023 mg/Kg body weight (minimum). Similarly, the maximum is about 2.3 mg/Kg body weight. If we assumed that the maximum weigh of a human to be treated with the ATS-albumin complex Is 70 Kg, then the upper limit would be 0.023×70=1.61 mg/70 kg body weight.

The present invention further contemplates that DTS may be used to treat other disease states from the same mechanism of up-regulating ERK-1 and ERK-2 pathways and Cadherin 5 to lead to memory enhancement and treatment of diabetic retinopathy, respectively. For instance, the hyperphosphorylation of ERK 1 and ERK 2 by DTS leads to the release of acetylcholine at the synaptic junction of brain cells which is fundamental to memory enhancement. Also DTS may stimulate stem cells (including granulocytes) from bone marrow. DTS additionally may increase thymus mass which leads to the production of more cytotoxic lymphocytes. The following subsections outline the mechanisms of action for the above and other disease states.

Implication of DTS in the Treatment of Auto-Immune Diseases

Data obtained from Human Mixed Lymphocytes Responses and CD3 dependent activation revealed that DTS down regulates Th-1 cytokines (11), to which the pro-inflammatory cytokines such as tumour necrosis factor-alpha (TNF-α), Interleukin-6 (IL-6), IL-1 (b) and IL-8 belong. While the Th-2 cytokines such as IL-4 was up-regulated. The preferential up-regulation of the IL-4 group of cytokines is an important observation since they are known to regulate the reticuloendothelial system (bone marrow functions) via the MAPkinase signalling pathway. DTS caused an increased in the production of granulocytes and erythrocytes (5;11), suggesting that it has an effect on bone marrow activity, possible on stem cells. Elevation in the levels of pro-inflammatory cytokines are associated with the on set of auto-immune diseases such as type-1 diabetes, rheumatoid arthritis, multiple sclerosis and lupus erythematosus (16;17).

DTS caused an increase in thymic weight in old mice (5;11), histological analyses of the thymic sections revealed that there was a proliferation of cells in the cortical region infiltrating the medulla (11). It is recognized that mitogenesis (MAPKinase/p21$^{ras}$) signalling pathway activated from the immuno-receptor tyrosine based activating motifs (ITAMS) within the CD3-TCR receptor complex is critical for positive/negative thymic cell production (18). Cancer patients' ability to generate T-lymphocytes is inversely related to their age, suggesting an indirect contribution from thymic involution (19). Similarly, the recovery of CD4+ cells is inversely related to age and was enhanced in patients with an enlarge thymus after chemotherapy (19). The functional status of the thymus is regulated by an immuno-endocrine-neurological input emerging from the hypothalamus-pituitary axis (19). The above finding is not surprising because of the fact that there is an interconnectivity of the immune, hormonal and nervous systems via the $Zn^{2+}$ dependent activating Sigma receptor which is mediated via a selective up-regulation of Th-2 cytokines e.g. IL-4 and IL-10 in conjunction with thymulin. Thus, potent cytotoxic effect of DTS on melanoma cells which carry Sigma receptors may support the fact that DTS could be a Sigma receptor agent. Presently, the Sigma receptor group of therapeutic drugs are being critically evaluated for treating/managing various forms of human leukocyte antigen-DR (HLA-DR) immune system dysfunction diseases such as diabetes, osteoarthritis, acquired immune deficiency syndrome (AIDS), asthma and cancers. In addition, the loss of a functional thymus or its absence is common among individuals with immuno compromised congenital diseases e.g. DiGeorge Syndrome (DGS), Chromosomal Breaking Syndromes (CBSs). The thymus is one of the sites producing cytotoxic lymphocytes (CTLs) which produced the serine protease enzyme granzyme B, a potent inducer of apoptosis in cancer cells and should be assessed. Thus, the thymic enlargement effect of DTS is worthy of detailed investigations.

The manipulation of various homing factors e.g. L-selectin-mAb LM1-3 and addressin-mAdCAM-1 and integrins such as alpha4beta7 as therapeutic targets on Peyer's patches dendritic cells is a rapidly expanding field in drug development against intestinal bowel diseases (IBD) e.g. colitis, colorectal carcinoma and Chrohn's disease (20;21). DTS caused an enlargement in Peyer's patches possible by an activation of cell proliferation. Thus, based on this finding we hereby proposed that the effect of DTS on the Peyer's patches should be elucidated with the hope of developing drugs against IBD.

Implication of the Up-Regulation of Cadherin-5

Dibenzyl trisulphide up-regulate the expression of cadherin-5 in human SH-SY$^5$Y$_{TRK-A}$ neuroblastoma cells pretreated with nerve growth factor (NgF) (11). Cadherin-5 is one of the important factors responsible for the stabilization of tight junctions. The loss of cadherin-5 mediated adhesion has been known to play an important role in the transition of epithelial tumours from a benign to an invasive state (22) and also in diabetic retinopathy. Thus, beside the direct toxic effect that DTS has on various forms of cancer cells, it also has the ability to inhibit their metastasis via the up-regulation of cadherin-5.

Implication of the Inhibitory Effect of DTS on Glycation.

From 1D $^1$H NMR studies DTS interact with Bovine Serum Albumin (BSA) at two main sites (a) at 1.6-3.4 ppm (multiplet) and (b) at 6.8 ppm (11). The first site could be attributed to an interaction up on the redox sensitive episolon-lysine envelope or on threonine. The second interaction signal is associated with the tyrosine envelope of the BSA (11). DTS was found to inhibit the binding of glucose to BSA (O'Connar personal communication). From the above findings the following hypothesis could be made; that DTS is interacting with the episolon-lysine residue in the BSA which suggest that the Amadori re-arrangement binding interaction was block. The Amadori interaction (glycation) between proteins and glucose is central to the generation of free radicals and destruction of proteins in the body and is the cause of various degenerative diseases such as arterial stiffening, cataract and neurological impairment (23). Therefore, it would appear that DTS could be developed as an anti-glycation molecule to halt the rapid progression of some degenerative diseases associated with free radicals and stress. It is also interesting to note that DTS is able to protect BSA from denaturation by 50.83% at 500 ng/mL (0.5 µg/mL) at pH 6.0 (11). This is a feature of non-steroidal anti-inflammatory drugs (24;25).

The Implication of DTS/Growth Factor Induced Hyper-Phosphorylation of MAPKinase (Erk 1 and Erk 2).

Dibenzyl trisulphide (DTS) hyperphosphorylate MAPKinase (erk 1 and erk 2) signalling induced by growth factors e.g. basic fibroblast growth factor (bFGF) by 30% at 1.0 µM and nerve growth factor (NgF) at 0.5 µM (7;11). The MAPkinase pathway is required for both long-term recognition memory and is associated with hyper-phosphorylation of erk 1 and erk 2 in different sub-region of the entorhinal cortex-hippocampal circuitry (26). In addition, the medial division of the medial geniculate nucleus and adjacent posterior intralaminar nucleus (MGm/PIN) cells that project to the lateral nucleus of the amygdale (LA) contribute to memory formation via erk 1 and erk 2 mediated transcriptions (27). It is also interesting to note that *P. alliacea*, from which DTS was isolated is used by the Amerindians of Latin America to improve memory (28).

Implication of DTS Induced Cell-Cell Attraction Possible Through a Polarization Effect on Ankyrins The present invention contemplates that DTS may be effective against many disorders, beyond even cancer. Erythrocytes (red blood cells, RBCs) separated from white blood cells (WBCs) interact with DTS in buffer induced cell-cell attraction with morphological changes without lysis at concentrations higher than those effective on cancer cells (11; 32). Spectrins are responsible for maintaining the morphological integrity of RBCs. Since DTS interacts with the tyrosyl residues on albumins e.g. bovine serum albumin (7;11), the present invention contemplates that the attraction induced by DTS among the RBCs could be on a polarized tyrosine rich domain such as ankyrins (32) and not a classical agglutination effect. 1D $^1$H NMR analyses revealed that the interaction between DTS and RBCs gave a similar aromatic signal to that observed for the DTS-BSA interaction (11), which suggest that tyrosine is also involved. Ankyrins are tyrosine rich protein domains on the surface of red blood cells (RBCs). Also, Ankyrins are present on various mammalian cell types including the membranes of nervous tissues, more specifically at the nodes of Ranvier. Thus, from these observations the present invention contemplates that DTS may activate ankyrin domains located on neurons which are capable of inducing attraction and growth in these cells by causing their redistribution to the plasma membrane with spectrin involvement (29). The above mentioned phenomenon involves the phosphorylation on tyrosine residues in the ankyrins (33), which is one of the central binding modes of DTS leading to the activation of the MAPKinase pathway (7;11). MAPKinase phosphorylation emerging from tyrosine residue situated on axons is one of the processes implicated in the regeneration/growth and possible repair of damaged neurons (34).

Therefore, the present invention contemplates that DTS should be able to increase the inter-surface connectivities between cells which have tyrosine residues in their ankyrins binding domains. Thus, in an infant where neuronal interconnectivity is rapidly developing is exposed to DTS the molecule may enhanced these cell-cell inter-connections; this may lead to enhancing the memory in the infant or child.

In addition, ankyrins are now found to be important in several demyelinating human diseases including Multiple Sclerosis. The functions of ankyrins are now been heavily examined on glial cells node formation. Further, DTS could be important in the activation of Dendritic cells, based on its ability to increase Peyer's patches and thymic masses, which is a rapidly expanding field in cancer chemotherapy.

DTS as a Pharmaceutical Prototype

Unlike the complex nature of some of the most promising anti-cancer drugs such as Taxol® and vinblastine; DTS is a simple molecule. Thus, several derivatives of DTS were produced at low cost, some with higher cytotoxic activities (10;30). In addition, DTS was transformed using 2-mercaptoethanol in methanol to methyl benzyl sulfonic anhydride, a molecule with potent anti-microbial and agrochemical activities (31).

Toxicity

Dibenzyl trisulphide did not have any effect on the sensitive process of protein biosynthesis in Starfish embryos (11). In addition, it seems to have some degree of selectivity to pathological cells, since it was found not to be toxic to the human fibroblast (HOFA) cell line over seven days(9). In addition, concentration of up to 30 mg/kg body weigh was not toxic to mice. DTS seems to activate the bone marrow at 10 mg/kg body weight since granulocytes differential count was increased by 50% (5).

Certain modifications and improvements will occur to those skilled in the art upon a reading of the foregoing description. By way of example, albumin may be substituted with other tyrosine containing peptides or proteins to serve as carrier molecules. The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the following claims.

REFERENCES

1. Vyas D M, Kadow J F. Paclitaxel: A unique tubulin interacting anti-cancer agent. Prog Med. Chem 1995; 32: 289-337.
2. Setzer C M, Werka J S, Irvine A K, Jackes B R, Setzer W N. Biological activity of rainforest plant extracts from far north Queensland, Australia. Research Signpost. In Biologically active natural products for the 21$^{st}$ Century. LAD Willimas (Ed.) 2006; 21-46.
3. Cohen P. Protein Kinase—the Major Drug Targets of the Twenty-first Century. Nat. Rev. Drugs Disc 2002; 1; 309.
4. Johnson L, Williams L A D, Roberts E. An insecticidal and acricidal polysulphide metabolite from the roots of *Petiveria alliacea* L. Pest. Sci 1997; 50; 228-232.
5. Williams L A D, The T L, Gardner M, Fletcher C K, Naravane A, Gibbs N, Fleishhacker R. Immunomodulatory activities of *Petiveria alliacea*. Phytotherapy Res. 1997; 11; 143-144.
6. Deschesnes R G, Huot J, Valerie K, Landry J. Involvement pf p38 in apoptosis associated membrane blebbing and nuclear condensation. Mol. Bio. of the Cell. 2001; 6; 1569-1582.
7. Rosner H, Williams L A D, Jung A, Kraus W. Disassembly of microtubules and inhibition of neurite outgrowth, neuroblastoma cell proliferation, and MAP kinase tyrosine dephosphorylation by dibenzyl trisulphide. Biochim Biophys Acta 2001; 1540: 166-177.
8. Mata-Greenwood E, Ito A, Westenburg H, Cui B, Mehta R G, Kinghom A D, Pezzuto J M. Discovery of novel inducer of cellular differentiation using HL-60 promyelocytic cells. Anticancer Res. 2001; 21: 1763-1770.
9. Williams L A D, Rosner H, Moller W, Kraus W. Antiproliferation/cytotoxic action of dibenzyl trisulphide, a secondary metabolite of *Petiveria alliacea*. Jamaican Journal of Science and Technology. 2004; 15: 54-60.
10. An H, Zhu J, Wang X, Xu X. Synthesis and anti-tumor evaluation of new trisulfide derivatives. Bioorganic and Medicinal Chemistry Letters. 2006; 16: 4826-4829.
11. Williams L A D, Rosner H, Conrad J, Moller W, Beifuss U, Chiba K, Nkurunziza J P, Kraus W. Selected secondary metabolites from Phytolaccaceae and their biological/pharmaceutical significance, Research Signpost. In Recent Research Development in Phytochemistry. 2002; 6: 13-68.
12. Williams L A D, Rosner H, Moller W, Conrad J, Nkurunziza J P, Kraus W. In vitro anti-proliferation/cytotoxic activity of sixty natural products on the human SH-SY5Y neuroblastoma cells with specific reference to dibenzyl trisulphide. West Indian Med. J. 2004; 53 (4) 208-219.
13. Franklin C C, Kraft A S. Conditional expression of mitogen-activated protein kinase (MAPK) phasphatase MKP-1 preferentially inhibits p38 MAKP and stress-activated protein kinase in U937 cells. Biological Chemistry. 1997; 272: 27: 16917-16923.
14. Price D T, Rocca G D, Guo C, Ballo M S, Schwinn D A, Luttrell L M. Activation of extracellular signal-regulated kinase in human prostate cancer. Journal of Urology. 1999; 162: 1537-1542.
15. Beltman J, McCormick F, Cook S J. The selective protein kinase c inhibitor RO-31-8220, inhibits mitogen-activated protein kinase phosphatase-1 (MKP-1) expression induces c-Jun expression, and activates Jun N-Terminal Kinase. Biological Chemistry. 1996; 271: 27018-27024.

16. Van de Meide P H, Schellenkens H. Cytokines and the immune response. Biotherapy. 1996; 8 (3-4): 243-249.
17. Licino J, Wong M L. The role of inflammatory mediators in the biology of major depression: central nervous system cytokines modulate the biological substrate of depression systems, regulate stress-responsive systems, and contribute to neurotoxicity and neuroprotection. Mol. Phsychiatry. 1999; 4 (4): 317-327.
18. Aberola-all J, Forbush K A, Seger R, Krebs E G, Perlmutter R M. Selective requirement of MAP Kinase activation in thymocytes differentiation. Nature. 1995; 373: 620-623.
19. Pawelec G, Remarque E, Barnett Y, Solana R. T cells and aging. Frontiers in Biosciences. 1998; 3: d59-99.
20. Min S Y, Parks K S, Cho M L, Kang J W, Cho Y G, Hwang S Y, Park M J, Yoon C H, Min J K, Lee S H, Park S H. Antigen-induced, tolerogenic CD11c+, CD11b+ dendritic cells are abundant in Peyer's patches durin the induction of oral tolerance to type 11 collagen and suppress experimental collagen-induced arthritis. Arthritis Rheum. 2006; 54 (3): 887-898.
21. Feral C C, Rose D M, Ham J, Fox N, Silverman G J, Kaushansky K, Ginsberg M H. Blocking the α4 integrinαpaxillin interaction selectively impairs mononuclear leukocyte recruitment to an inflammatory site. J. Clin. Invest. 2006; 116: 715-723.
22. Hazan R B, Phillips G R, Qiao R F, Norton L, Aaronson S. Exogenous expression of N-cadherin in breast cancer cell induces cell migration, invasion and metastasis. The Journal of Cell Biology. 2000; 148: 779-790.
23. Kawabata T, Packer L. α-lipoate can protect against glycation of serum albumins but not low density lipoproteins. Biochemical and Biophysical Research Communications. 1994; 203 (1): 99-104.
24. Grant N H, Album. H E, Kryzanauska C. Stabilization of serum albumin by anti-inflammatory drugs. Biochemical Pharmacology. 1970; 19: 715-722.
25. Williams L A D, Vasquez E A, Milan P P, Zebitz C, Kraus W. In vitro anti-inflammatory and anti-microbial activities of phenylpropanoids from Piper betle (Piperaceae) In Proceeding of the Phytochemical Society of Europe: Natural products in the new millennium: Prospects and industrial application. A P Rauter, P B Palma, J Justino, Araujo M E, Santos S P (Eds). Kluwer Academic Publisher, Dordrecht. The Netherlands. 2002; 74: 221-227.
26. Kelly A, Laroche S, Davis S. Activation of mitogen-activated protein kinase/extracellular signal regulated kinase in hippocampal circuitry is required for consolidation and reconsolidation of recognition memory. The Journal of Neuroscience. 2003; 23:(12): 5354-5360.
27. Apergis-Schoute A M, Debiec, J, Doyere V, LeDoux J E, Schafe G E. Auditory fear conditioning and long term potentiation in lateral amygdale require ERK/MAPKinase signalling in the auditory Thalamus: A role for presynatic plasticity in fear system. The Journal of Neuroscience. 2005; 24: 5730-5739.
28. http://www.rain-tree.com/anamu.htm (last visited Dec. 1, 2006)
29. Dubreuil R R, MacVicar G, Dissanayake S, Liu C, Homer D, Hortsch M. Neuroglian-mediated cell adhesion induces assembly of the membrane skeleton at cell contact sites. The Journal of Cell Biology. 1996; 133: 647-655.
30. X, An H, Wang X. Substituted organosulfur compounds and methods of using thereof. US Published Patent Application No. 2005/0261321; 2005.
31. Williams L A D, Vasquez E, Klaiber I, Kraus W, Rosner H. A sulfonic anhydride from dibenzyl trisulphide with agro-chemical activities. Chemosphere. 2003; 51: 701-706.
32. Williams L A D, Smikle M, Gibbs N, Barton E N, Igietseme J U, Whittaker J A, Thompson W. Mitogenic and erythrocytic effects of Dibenzyl trisulphide (DTS). 1997; Abstract of Paper Presented at the Fifth Conference of the Faculty of Medical Sciences, University of the West Indies, Mona, October 2-3, Kingston, Jamaica
33. Garver T D, Ren Q, Tuvia S, Bennett V. Tyrosine phosphorylation at site highly conserved in the L1 family of cell adhesion molecules abolishes ankyrin binding and increase lateral mobility of neurofascin. J. Cell. Biol. 1997; 137:3: 703-714.
34. Whittard J D, Sakurai T, Cassella M R, Gazdoiu M, Felsenfeld D P. MAPKinase pathway-dependent phosphorylation of the L1-CAM ankyrin binding site regulates neuronal growth. Mol. Biol. Cell. 2006; 17: 2696-2706.

What is claimed is:

1. A method for providing an anti-cancer treatment comprising the steps of:
providing an organosulfur composition having dibenzyl trisulfide (DTS) combined with an albumin comprising mixing a DTS solution with an albumin solution so that a resulting stock solution contains an excess of about 6 moles of DTS for each mole of albumin, thereby formulating the DTS combined with the albumin to have an increased cytotoxic activity toward cancer cells about 2500 times greater than the cytotoxic activity of DTS without albumin; and
administering the formulation in a therapeutically effective amount to a patient having the cancer cells.

2. The method of claim 1, wherein the albumin is bovine serum albumin (BSA).

3. The method of claim 1, wherein the step of administering includes intravenous administration to the patient.

4. The method of claim 1, wherein the step of administering includes topical administration to the patient.

5. The method of claim 1, wherein the step of administering includes oral administration.

6. The method of claim 1, wherein the step of administering includes targeted administration to the cancer cells.

7. The method of claim 1, wherein the formulation dosage for administration is predetermined based upon data specific to each patient.

8. The method of claim 2, wherein the formulation dosage is between about 0.025 mg/kg and about 4.5 mg/kg body weight.

* * * * *